(12) United States Patent
Orbay et al.

(10) Patent No.: US 11,096,734 B2
(45) Date of Patent: Aug. 24, 2021

(54) DEVICES AND METHODS FOR ORTHOPEDIC SURGERY REQUIRING FASTENERS OF MULTIPLE LENGHTS

(71) Applicant: Skeletal Dynamics, Inc., Miami, FL (US)

(72) Inventors: Jorge L. Orbay, Miami, FL (US); Antonio R. Orbay-Cerrato, San Juan, PR (US); Dennis J. Moreno, Miami, FL (US); Robert Richards, New Haven, CT (US); Erik Carlson, Newington, CT (US)

(73) Assignee: SKELETAL DYNAMICS, INC., Miami, FL (US)

(*) Notice: Subject to any disclaimer, the term of this patent is extended or adjusted under 35 U.S.C. 154(b) by 66 days.

(21) Appl. No.: 16/530,506

(22) Filed: Aug. 2, 2019

(65) Prior Publication Data

US 2019/0365447 A1    Dec. 5, 2019

Related U.S. Application Data

(63) Continuation of application No. 14/729,589, filed on Jun. 3, 2015, now Pat. No. 10,383,673.

(60) Provisional application No. 62/007,163, filed on Jun. 3, 2014.

(51) Int. Cl.
*A61B 17/88* (2006.01)
*A61B 90/00* (2016.01)

(52) U.S. Cl.
CPC .... *A61B 17/8863* (2013.01); *A61B 2090/061* (2016.02)

(58) Field of Classification Search
CPC ... A61B 17/8863; A61B 17/88; A61B 17/866; A61B 17/7092
See application file for complete search history.

(56) References Cited

U.S. PATENT DOCUMENTS

| 2003/0229354 | A1* | 12/2003 | Schmieding | A61B 17/866 606/99 |
| 2004/0138662 | A1* | 7/2004 | Landry | A61B 17/7037 606/86 A |
| 2010/0111631 | A1* | 5/2010 | Trieu | B23D 43/02 409/179 |
| 2014/0090527 | A1* | 4/2014 | Behlen | A61B 17/8863 83/13 |
| 2014/0257413 | A1* | 9/2014 | Appenzeller | A61B 17/866 606/316 |
| 2014/0277180 | A1* | 9/2014 | Paolino | A61B 17/8605 606/291 |

* cited by examiner

*Primary Examiner* — Julianna N Harvey
(74) *Attorney, Agent, or Firm* — Lott & Fischer, P.L.

(57) ABSTRACT

Disclosed are devices and methods used to customize the length of fasteners used during orthopedic surgeries, comprising creating a hole of the desired depth in a bone, measuring the depth of the hole using a depth measuring device, calculating, using the depth measuring device, the optimal length dimension of the fastener, transferring the calculated fastener optimal length dimension to a fastener cutting device, inserting a fastener having a length exceeding the optimal length dimension into the fastener cutting device, and cutting the fastener to the optimal length dimension using the fastener cutting device.

5 Claims, 7 Drawing Sheets

DEVICES AND METHODS FOR ORTHOPEDIC SURGERY REQUIRING FASTENERS OF MULTIPLE LENGHTS

CLAIM OF PRIORITY

This application is a continuation of U.S. non-provisional patent application Ser. No. 14/729,589 filed on Jun. 3, 2015, now U.S. Pat. No. 10,383,673, which claims priority to U.S. Provisional Patent Application Ser. No. 62/007,163 filed on Jun. 3, 2014, the contents of which are incorporated herein by reference.

FIELD OF INVENTION

The invention relates generally to fasteners for use in surgical procedures and in particular to methods and devices used to customize the length of fasteners used during orthopedic surgeries.

BACKGROUND OF THE INVENTION

Orthopedic surgeons require many different lengths of fasteners to accommodate all of the different procedures and anatomy that they encounter during surgery. Currently, manufacturers meet the needs of surgeons by supplying them with many different size fasteners that accommodate a range of lengths that the surgeon is likely to require. This means that inventories of fasteners have to be large to offer all the sizes that may be required. Even with large inventories, a surgeon is always forced to choose from the discrete number of sizes available which means he is often not getting the exact length he wants. Too long a fastener length can lead to soft tissue irritation on the protruding end and too short a fastener length can result in poor screw purchase.

Currently, fasteners of different discrete lengths are delivered to the surgeon in the operating room in two alternate modes:

(A.) As part of a "surgical tray" containing surgical appliances (such as plates), fasteners and instruments expected to be needed during surgery. The surgical tray and its contents are sterilized prior to every use in the operating room. Normally the fasteners of many different lengths will be included in a "screw caddy" inside the tray. These caddies typically carry tens of fasteners, of which only a small fraction (5% or less) are used in one particular surgery. The unused fasteners remain in the caddy for further sterilization and use in subsequent surgeries.

(B.) As part of a "pre-sterilized kit" that includes a surgical appliance, a set of disposable instruments and a reduced number of fasteners of different lengths. The proper kit is selected by determining the plate (or other surgical appliance) size and orientation (right or left) using a template. The surgeon will then select and use fasteners of the proper length. The unused fasteners are disposed of at the end of the surgery together with the disposable instruments.

The disadvantage of the surgical tray mode of delivery is that each tray carries a great number of fasteners of different lengths of which only a few are used in a case. This reflects in a high cost idle inventory, given the relatively high cost of surgical grade fasteners.

On the other hand, the disadvantage of the pre-sterilized kit mode of delivery is that, even with a reduced number of fasteners of different lengths in each kit, the number of fasteners actually used in surgery is still a fraction of the fasteners available and the fact that, at the end of the surgery, the unused fasteners are disposed of as waste.

An additional disadvantage inherent in both modes is that fasteners are provided in discrete lengths, usually in 1 or 2 mm increments, thereby limiting the choice of fasteners to those particular lengths.

SUMMARY OF THE INVENTION

An object of the instant invention is to overcome the disadvantages of the surgical tray mode (high cost of idle inventory) and the pre-sterilized kit mode (disposal of costly unused fasteners) by providing fasteners that can be cut to the exact desired length while in the operating room.

The method of the present invention utilizes two devices and a plurality of "long fasteners" or a "blanks" to be cut to the desired length. Long fasteners are fasteners of the desired diameter, head type and tread pitch, which have a length that is longer than the length desired for use by the surgeon.

The first device is a depth gauge used by the surgeon to measure the length of a needed fastener. The depth gauge is adapted to acquire and transfer information to the second device about the required length of a fastener when the surgeon removes the gauge after insertion into a bone.

The second device is a fastener cutting device that cooperates with the depth gauge to acquire the fastener length information and receives a long fastener or portions of a long fastener of length longer than the required length and cuts it/them to the desired length. The second device can also, optionally, be used to provide a desired finish (such as de-burring, cutting flutes, or rounding off) or to form a head on the cut end of the screw.

DETAILED DESCRIPTION OF THE INVENTION

The method for customizing the length of a fastener in accordance with the present invention is comprised of the following steps:

Step one: the user (surgeon, surgical assistant, nurse, etc.) is provided with a depth gauge or other depth measuring device and a fastener cutting device, both in accordance with the present invention.

Step two: the user inserts the depth gauge into a hole drilled on a patient's bone that is to be fixed or fitted with a custom length fastener.

Step three: the user operates the depth gauge mechanism to engage the far cortex of the patient's bone, thereby determining the depth of the hole and the desired final length of the fastener. The depth gauge retains the information about the desired length of the fastener and optionally displays a visual, audible or some other form of cue indicating said length.

Step four: the user removes the depth gauge from the hole and places it in physical, electronic or other form of communication with the fastener cutting device and transfers or transmits to the cutting device the desired length information.

Step five: based on the transferred desired length information, the cutting mechanism on the fastener cutting device is configured for cutting a fastener in the desired custom length.

Step six: an over-length fastener "blank" is inserted into the fastener cutting device and cut to the desired length. It should be noted here that the step of inserting the blank into the fastener cutting device can be performed at any time prior to cutting, irrespective of whether the previous steps have already been performed.

Step seven: the fastener cutting device releases a completed fastener in the desired length.

In one embodiment, the cutting device cuts the fastener at its leading (thread) end, and using a finishing tool, de-burrs the end and, if needed, forms a rounded tip and/or cutting flutes. In an alternate embodiment, the cutting device cuts the trailing, or head, end of the fastener and forms a head with the desired characteristics for driving the fastener.

In a further alternate embodiment the long fastener is provided in two parts: a.) a trailing part consisting of a head and a spike and b.) a cannulated, threaded, leading part adapted to lockingly receive the spike. In this alternate embodiment the cutting device cuts the trailing part at the end opposite the head and the leading part at the end opposite to the threaded end and assembles the two parts together, delivering a fastener of the desired length. The leading and trailing parts may be made of different materials (e.g. leading part of biocompatible PEEK and trailing part of biocompatible metal).

Examples of the depth gauge and cutting device used for practicing the method of the present invention are described in further detail below.

Figure 1:
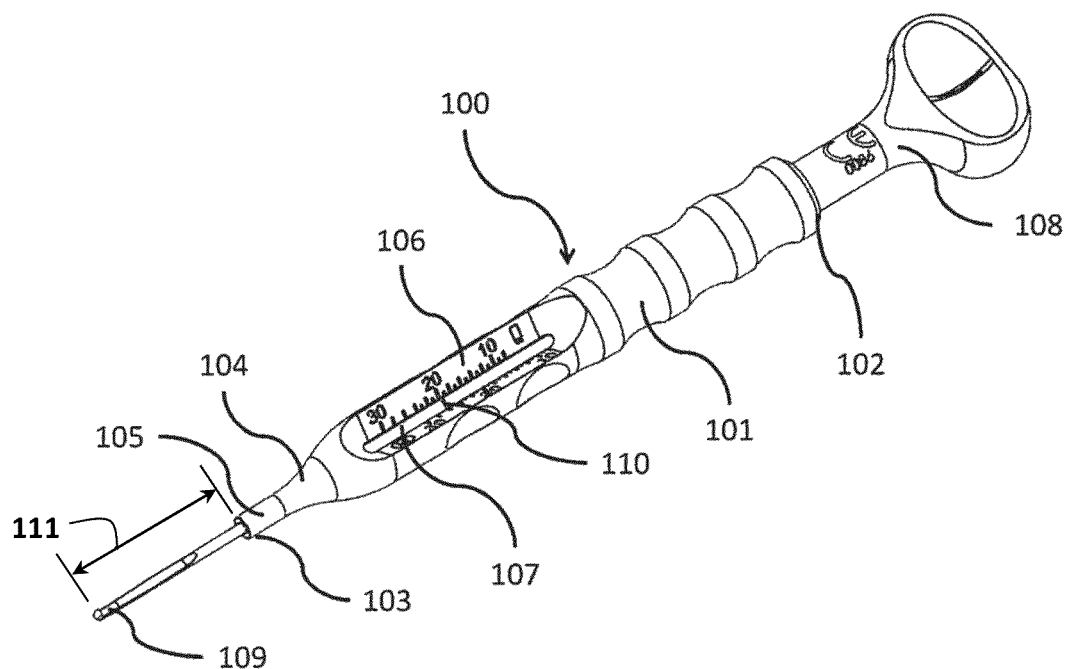
FIG. 1 is a surgical depth gauge in accordance with the present invention.

Referring to FIG. 1, the surgical depth gauge (100) comprises a sleeve (101) having an open proximal end (102) and an open distal end (103). The distal end (103) may optionally comprise a cap (104) to facilitate disassembly of the depth gauge for cleaning. The cap (104) may be screwed or snapped on to the sleeve (101). The distal end (103) of the sleeve has a diameter (105) that is greater than the widest hole which the gauge is designed to measure and thus prevents the sleeve from penetrating the hole during measurements. The sleeve (101) may also, optionally, include a scale (106) to indicate the depth of the hole being measured.

The sleeve (101) houses an inner element (107) which also has proximal (108) and distal (109) ends and which has a substantially longer length than the sleeve. The distal end (109) of the inner element (107) (also referenced as the "probe end") comprises a narrow probe tip which has a diameter that is smaller than the narrowest hole which the gauge is designed to measure and thus enables the probe end (109) to penetrate all holes during measurements. The probe end (109) extends beyond the opening at the distal end (103) of sleeve (101). The proximal end (108) of inner element (107) similarly extends past the proximal end (102) of the sleeve (101) and may optionally include a scale (106) which can be used to indicate, in cooperation with a reference marker (110) on the inner element (107), the length (111) of the protruding portion of the probe end (109). If a scale (106) is included, the scale is calibrated to indicate a number adjacent to the reference marker (110) which is equal to the length (111) of the protruding portion of the probe end (109) in a known unit of length (e.g. millimeters, inches, etc.)

The sleeve (101) and inner element (107) of depth gauge (100) are adapted to closely cooperate with each other so that the inner element (107) can travel longitudinally within the sleeve (101) yet there is enough friction between the sleeve (101) and inner element (107) that a nominal amount of force must be applied to the inner element (107) in order to make it move relative to the sleeve (101). There may optionally be included a locking mechanism (not shown) which locks the inner element (107) and sleeve (101) relative to each other so as to prevent inadvertent movement of the inner element (107) once a depth measurement has been taken.

The depth gauge (100), in another embodiment (not shown), could optionally include an electronic encoder/transmitter which is calibrated to measure the protruding portion of the probe end in one or more known units of length (e.g. millimeters). The electronic encoder could also be enabled to electronically store in memory, display and/or wirelessly transmit the measured length of the protruding portion of the probe end for use by the fastener cutting device.

In order to measure the depth of a hole using the depth gauge (100) of the present invention, the depth gauge (100) would be prepared for measurement by extending the probe end (109) of the inner element (107) to its maximum length. This is done by depressing the proximal end (108) of the inner element into the sleeve (101) until it can travel no further. The probe end (109) can then be inserted into the hole until its tip engages the deepest part of the hole. The sleeve (101) is then be pushed in the direction of the hole until the distal end of the sleeve (103) touches the opening of the hole and cannot be pressed further. If the depth gauge is equipped with a scale (106), the readout on the scale, relative to the reference marker (110), indicates the depth of the hole.

If the depth gauge is equipped with a locking mechanism (not shown), it can be activated at this point in order to lock the inner element and sleeve relative to each other and preserve the measurement. Similarly, if the depth gauge is equipped with an electronic encoder/transmitter (not shown), it can be activated at this point in order to store and transmit the depth information to the cutting device (FIG. 2, 200) of the present invention.

Referring next to FIGS. 2-5, the cutting device (200) of the present invention is comprised of a stationary base (201) having a longitudinal axis (202), a ratchet rack (204) affixed to the upper surface of the stationary base, a fastener holding table (203) slidably mounted directly above the ratchet rack (204) and slidable along the longitudinal axis (202), a fastener length reference indicator (205) affixed to stationary base and having a pointer (206) in close proximity to the top surface (207) of the fastener holding table, and a cutting bridge assembly (208) mounted adjacent to the fastener holding table (203) further distally in the longitudinal direction.

The ratchet rack (204) engages a ratchet catch (210) on the fastener holding table (203) which permits the screw holding table to move only in the direction along the longitudinal axis (202) relative to the cutting bridge assembly (208). If the user desires to slide the fastener holding table (203) in the longitudinal direction relative to the cutting bridge assembly (208), he or she must operate a ratchet release button (219) which disengages the ratchet catch (210) from the ratchet rack (204) and allows the fastener holding table (203) to slide in either direction.

Figure 3:
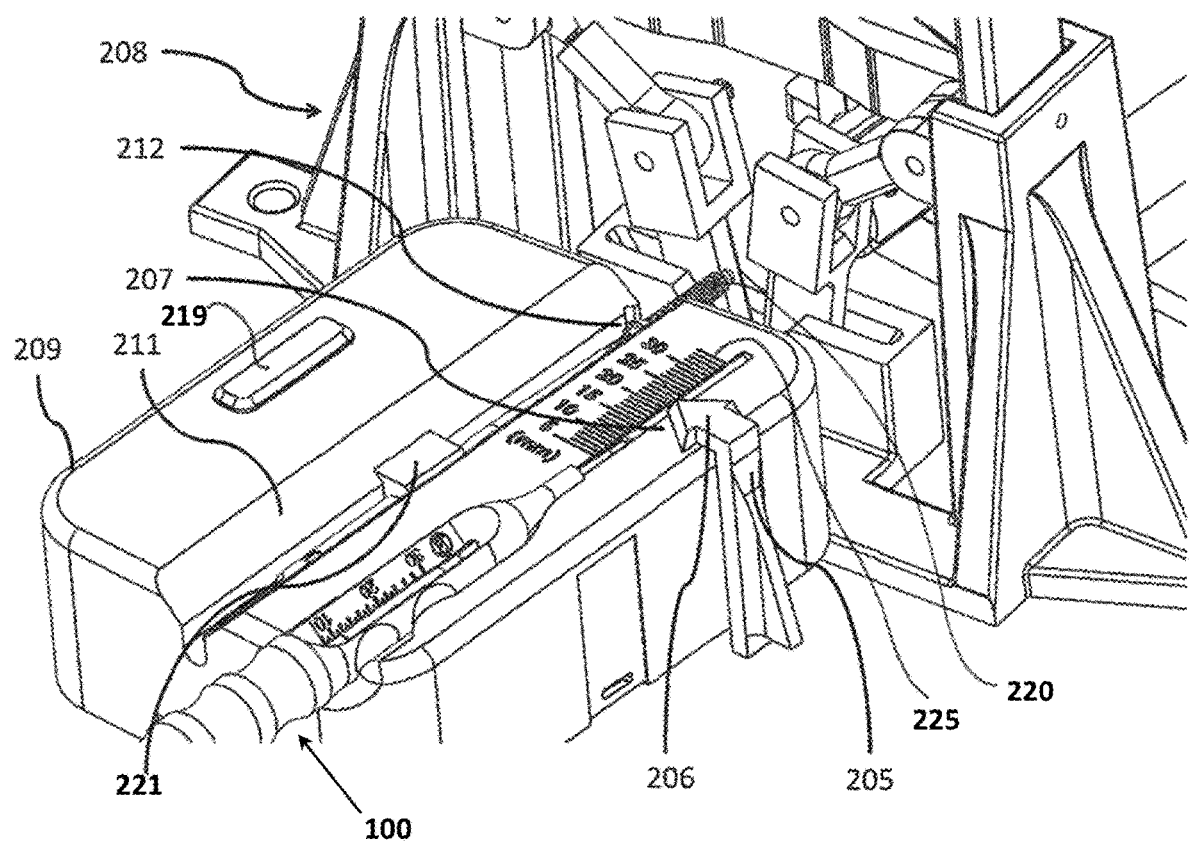
FIG. 3 is a detail view of a cutting device in accordance with the present invention illustrating the fastener holding table and fastener length reference indicator.
Figure 4:
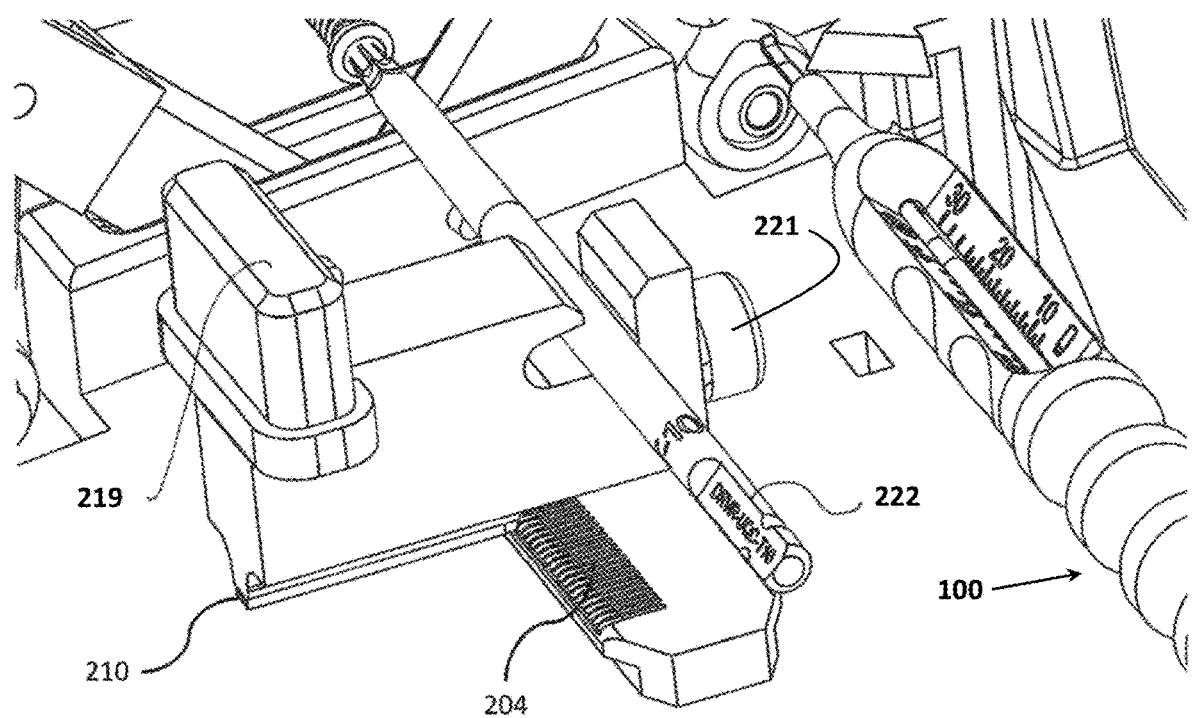
FIG. 4 is a detail view of a cutting device in accordance with the present invention with the fastener holding table partially removed to illustrate the ratchet rack and catch.
Figure 5:
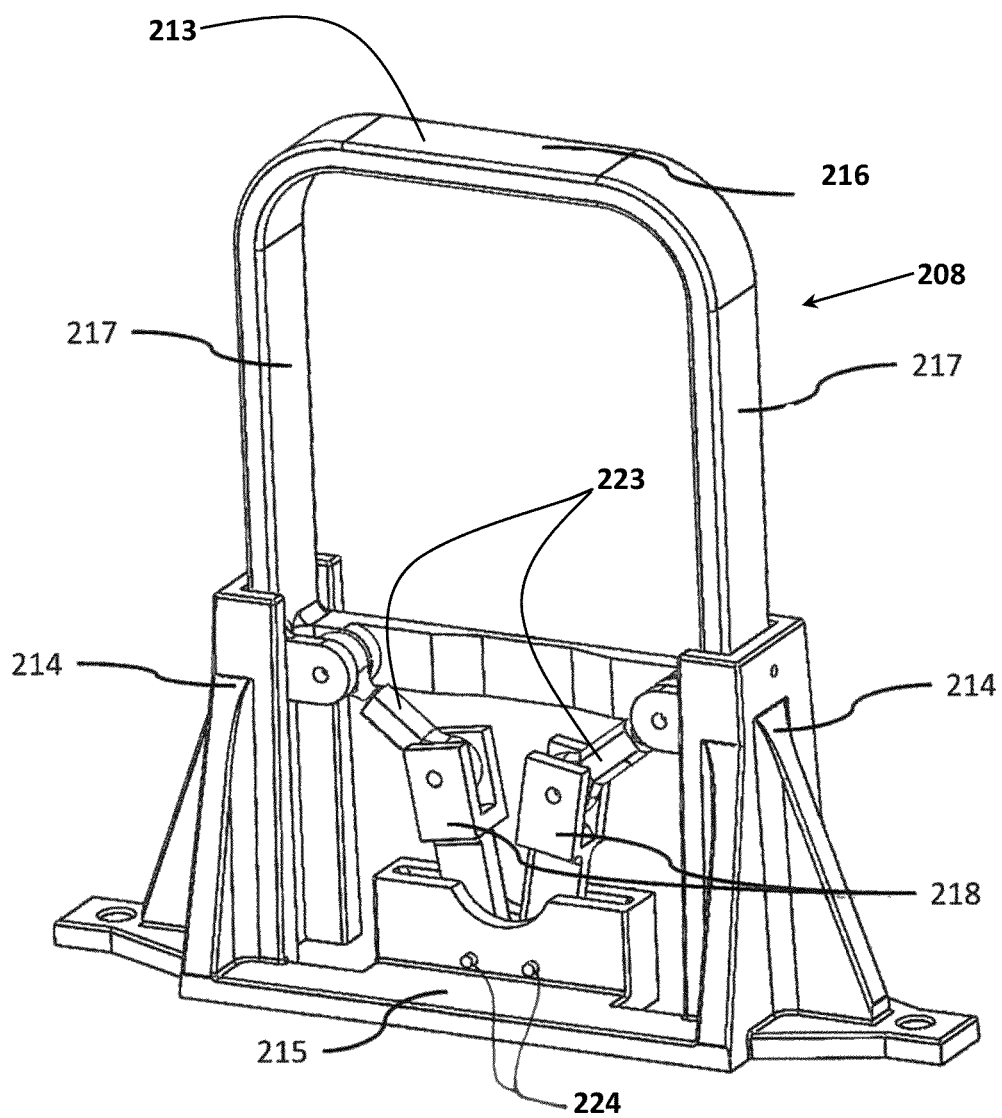
FIG. 5 is a general view of a cutting bridge assembly in accordance with the present invention in its initial position.

The fastener holding table's top surface (207) is equipped with a fastener holding channel (211) which is adapted to hold a long fastener or blank (220). The end (212) of the fastener holding channel closest to the cutting bridge assembly (208) is adapted to securely hold the head of the blank (220) so that the end to be cut extends beyond the end of the fastener holding table (203) into the direction of the cutting bridge assembly (208). As shown in FIGS. 3 and 4, the fastener holding channel (211) may be adapted to accommodate a driver (222) to more securely hold the blank (220) in place. A driver holding lock (221) may also optionally be provided to more securely hold the driver (222) in place on the fastener holding channel (211).

The cutting bridge assembly (208) comprises an operating handle (213) which is retained by dual vertical guide rails (214) affixed to the stationary base (215). The vertical guide rails (214) enable the operating handle (213) to travel up and down with respect to the stationary base (215). The operating handle (213) has an inverted "U" shape with a single horizontal member (216) and twin vertical members (217) that slidably engage the guide rails (214). The twin vertical members (217) are coupled with push rods (223) that, in turn, engage twin cutting blades (218) which pivot about pivot points (224) that are affixed to the stationary base. The cutting bridge assembly (208) is aligned relative to the longitudinal axis (202) of the stationary base (201) such that the cutting blades (218) pivot along a plane that is perpendicular, or optionally oblique at an angle between 0 and 30 degrees, relative to the longitudinal axis (202) of the stationary base (201).

Figure 6A:
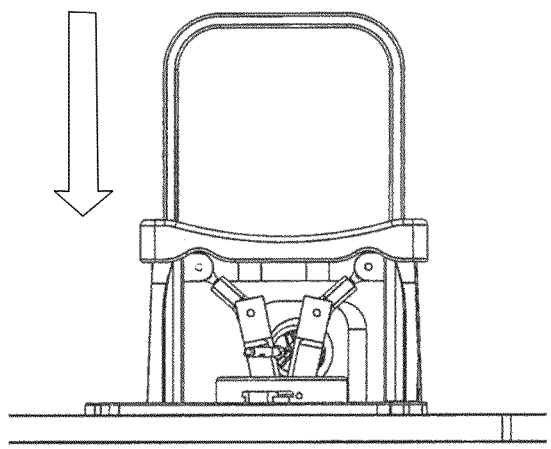
FIGS. 6A-6C illustrate the cutting sequence of a cutting bridge assembly in accordance with the present invention.
Figure 6B:
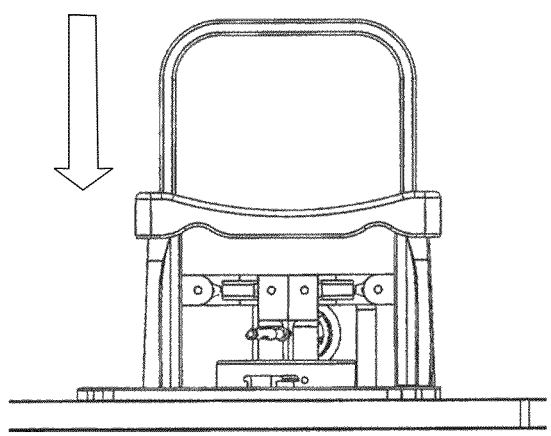
Figure 6C:
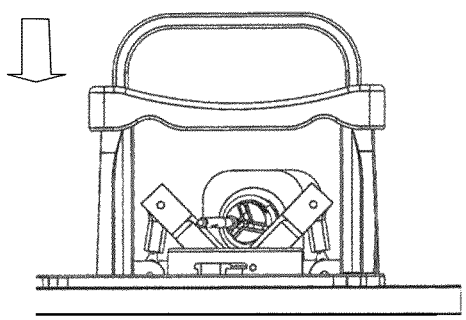

Referring next to FIGS. 6A-6C, the cutting operation commences in FIG. 6A with the operating handle in its uppermost position, the push rods in a diagonal position, with their outermost ends pointing upwards, and the cutting blades in the fully open position. As the operating handle is pressed down, its vertical members begin to push the push rods inward which, in turn, begin to pivot the blades to the closed cutting position. As the handle reaches a mid-point position (FIG. 6B), the push rods are in a horizontal position and the cutting blades are urged together to their maximum cutting positions. As the operating handle continues to be pressed downward, the push rods travel past their horizontal position and the cutting blades begin to open once again. At the end of the cutting operation (FIG. 6C), with the operating handle fully depressed, the cutting blades are, once again, at their fully open position and the push rods are again in a diagonal position, but with their outermost ends pointing downward. It is noted that at the end of the cutting operation, the cutting blades are sufficiently separated so as to allow a finishing tool (discussed below) to be placed between them without interference and to engage the cut end of the fastener.

Referring back to FIG. 3, the fastener holding table's top surface (207) is further equipped with a scale (225) that cooperates with the pointer (206) of the length reference indicator (205) and indicates a distance between the end of the holding table and the cutting plane of the cutting blades. The scale (225) is calibrated so that when a fastener is cut using the cutting bridge assembly, the indicated length is the total length of the fastener after the cutting operation is completed.

Figure 2:
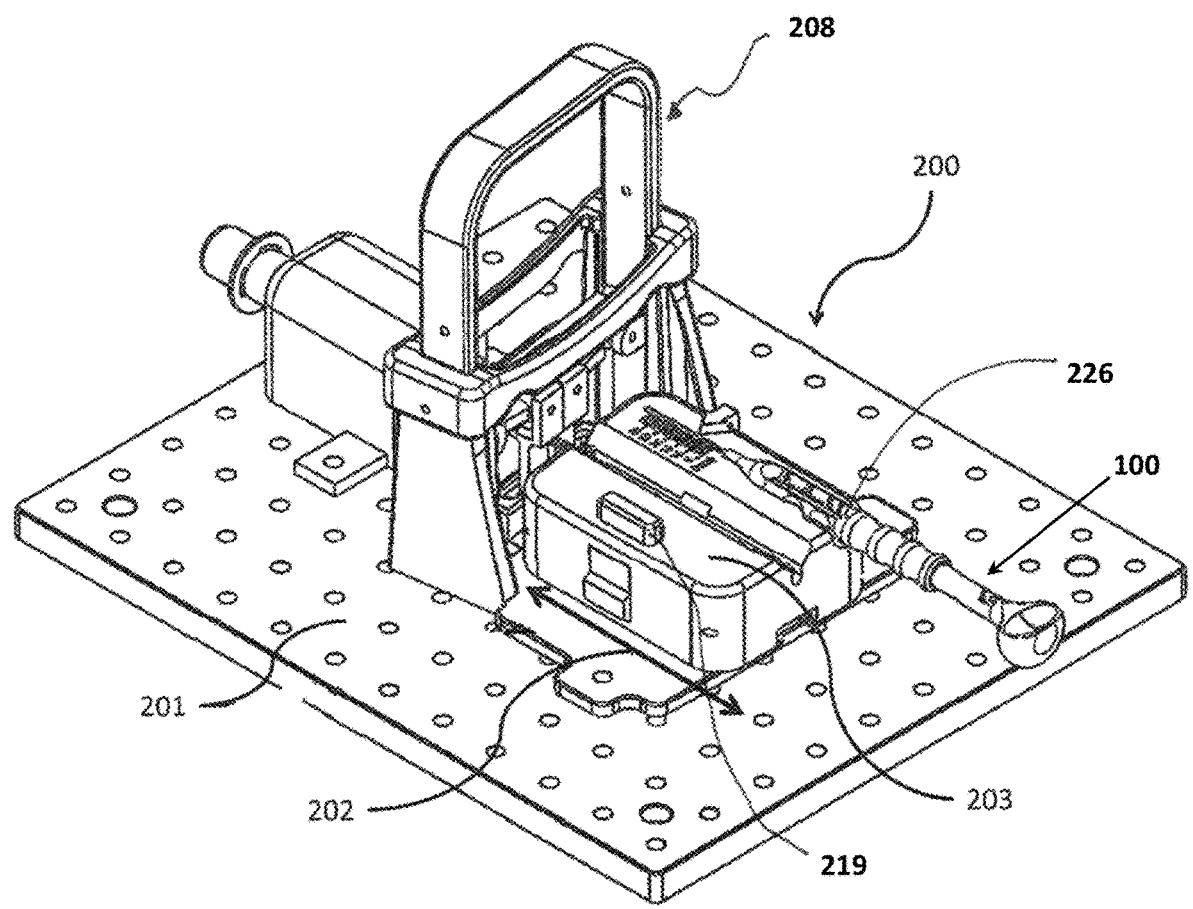
FIG. 2 is a general view of a cutting device in accordance with the present invention.

In order to cut a fastener to a custom length using the depth gauge (100) and cutting device (200) of the present invention, the user would first measure the depth of a hole drilled into a bone using the depth gauge. The user would then transfer the measured depth to the cutting device. This could be done manually, by sliding the fastener holding table until the pointer of the length reference indicator indicates the same length as the scale on the depth gauge. Alternatively, as shown in FIG. 2, the screw holding table may be equipped with an orifice or channel (226) into which the end of depth gauge (100) can be inserted, and as the depth gauge is inserted, it would urge the screw holding table towards the cutting blades. Once the correct depth is set on the cutting device, the end of the depth gauge would reach the pointer (206) of the length reference indicator (205). The operator would then stop urging the screw holding table towards the cutting blades. In an alternative embodiment, the pointer (206) could be equipped with a stop (not shown) which would prevent the depth gauge (100) from moving further and thus assure the cutting depth is accurately set.

In an alternative embodiment, the fastener holding table (203) could be equipped with a wireless receiver and a stepper motor. The wireless receiver could electronically receive the length indication from the depth gauge and control the stepper motor to move the fastener holding table to the proper position for the desired length.

Once the desired length has been set on the cutting device, the cutting operation could be completed as shown in FIGS. 6A-6C by depressing the operating handle and effecting the complete cutting cycle. The cut fastener could then be removed and used in surgery on the designated hole.

Figure 7:
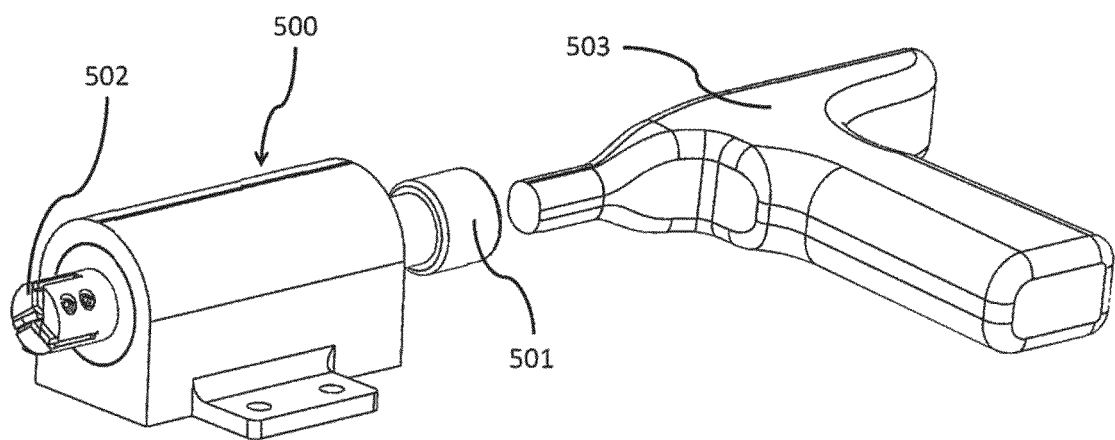
FIG. 7 illustrates a finishing tool in accordance with the present invention shown together with a hand-held drill.

In an alternative embodiment, shown in FIG. 7, the cutting device may optionally be equipped with a finishing tool (500) situated behind the cutting bridge and in direct longitudinal alignment with the fastener being cut to length. The finishing tool (500) may consist of a rotary de-burrer or flute cutter (502) which is driven by a rotary motor (not shown) or equipped with a chuck (501) to be engaged by a hand-operated drill (503). Once the fastener is cut to the desired length, the fastener holding table could be further longitudinally advanced past the cutting plane of the cutting blades until it engages the finishing tool (500). Alternatively, the finishing tool may be equipped with rails (not shown) that enable it to be advanced in the direction of the cut fastener, past the cutting plane of the cutting blades until it engages the cut end of the fastener. The finishing tool would then be activated either through its rotary motor or by a drill (503), to finish the cut end of the fastener. The cut fastener could then be removed and used in surgery on the designated hole.

Although the invention is described herein, various modifications and structural changes may be made therein without departing from the spirit of the invention and within the scope and range of equivalents of the claims.

We claim:

1. A method for customizing the length of a fastener to be fitted to a bone during a surgery, said method comprising the steps of:

creating a hole of a desired depth in said bone;

measuring the depth of said hole using a depth gauge, the depth gauge comprising an electronic encoder;

the electronic encoder adapted to transmit the measured depth of said hole;

transmitting the measured hole depth from the depth gauge to a fastener cutting device;

adjusting the fastener cutting device to cut said fastener to a desired length dimension based on said transmitted measured hole depth;

inserting a fastener having a length exceeding said desired length dimension into said fastener cutting device; and cutting said fastener to said desired length dimension using said fastener cutting device.

2. The method of claim 1 wherein said hole is drilled into said bone.

3. The method of claim 1 wherein the fastener cutting device further comprises a wireless receiver, and wherein said depth gauge is adapted to wirelessly transmit the measured hole depth to the wireless receiver of the fastener cutting device.

4. The method of claim 1 wherein said depth gauge further comprises storage memory and wherein the depth gauge stores the measured hole depth in said storage memory.

5. The method of claim 1, wherein said depth gauge is adapted for displaying the measured hole depth.

\* \* \* \* \*